(12) United States Patent
Futashima et al.

(10) Patent No.: US 11,749,426 B2
(45) Date of Patent: Sep. 5, 2023

(54) METHOD FOR PRODUCING BIOELECTRODE

(71) Applicant: NOK CORPORATION, Tokyo (JP)

(72) Inventors: Ryo Futashima, Fujisawa (JP); Yasushi Sugiyama, Fujisawa (JP); Toru Uda, Fujisawa (JP); Takumi Yoshitomi, Fujisawa (JP)

(73) Assignee: NOK CORPORATION

( * ) Notice: Subject to any disclaimer, the term of this patent is extended or adjusted under 35 U.S.C. 154(b) by 507 days.

(21) Appl. No.: 16/854,963

(22) Filed: Apr. 22, 2020

(65) Prior Publication Data

US 2020/0251258 A1 Aug. 6, 2020

Related U.S. Application Data

(63) Continuation of application No. PCT/JP2019/022455, filed on Jun. 6, 2019.

(30) Foreign Application Priority Data

Jun. 15, 2018 (JP) .................................. 2018-114504

(51) Int. Cl.
*H01B 13/00* (2006.01)
*H01B 1/22* (2006.01)
(Continued)

(52) U.S. Cl.
CPC .......... *H01B 13/0036* (2013.01); *A61B 5/291* (2021.01); *A61B 2562/0215* (2017.08);
(Continued)

(58) Field of Classification Search
CPC .................. H01B 13/0036; H01B 1/22; A61B 2562/0215; A61B 2562/125; A61B 5/291; B05D 1/18; B05D 5/12
(Continued)

(56) References Cited

U.S. PATENT DOCUMENTS

| | | | | |
|---|---|---|---|---|
| 3,420,223 A | * | 1/1969 | Day .......................... | A61B 5/25 600/397 |
| 3,669,110 A | * | 6/1972 | Low ....................... | A61B 5/324 600/397 |

(Continued)

FOREIGN PATENT DOCUMENTS

| | | |
|---|---|---|
| EP | 3 482 683 A1 | 5/2019 |
| JP | H10-338799 A | 12/1998 |

(Continued)

OTHER PUBLICATIONS

Gao et al. "Investigation on Permeation properties of liquids into HTV silicon rubber materials", IEEE Transactions of Dielectrics and Electrical Insulation, IEEE Service Center, Piscataway, NJ—vol. 21, No. 6 pp. 2428-2437 (Year: 2104).*

(Continued)

*Primary Examiner* — Brian K Talbot
(74) *Attorney, Agent, or Firm* — Harness, Dickey & Pierce, P.L.C.

(57) ABSTRACT

A method is provided for producing a bioelectrode capable of reducing potential variation noise due to a polarization voltage. The method for producing the bioelectrode comprises forming an electrically conductive rubber body containing a silicone rubber and a silver powder, and immersing the electrically conductive rubber body in an inorganic salt-containing solution at 70° C. or more and 180° C. or less.

4 Claims, 14 Drawing Sheets

(51) Int. Cl.
 *A61B 5/291* (2021.01)
 *B05D 5/12* (2006.01)
 *B05D 1/18* (2006.01)

(52) U.S. Cl.
 CPC .......... *A61B 2562/125* (2013.01); *B05D 1/18* (2013.01); *B05D 5/12* (2013.01); *H01B 1/22* (2013.01)

(58) Field of Classification Search
 USPC ........................................ 427/2.1, 58, 430.1
 See application file for complete search history.

(56) References Cited

U.S. PATENT DOCUMENTS

| | | | | |
|---|---|---|---|---|
| 3,752,151 | A * | 8/1973 | Robichaud | A61B 5/25 600/394 |
| 3,982,529 | A * | 9/1976 | Sato | A61B 5/25 600/397 |
| 3,989,036 | A * | 11/1976 | Sasamori | A61B 5/282 600/397 |
| 4,082,087 | A * | 4/1978 | Howson | A61B 5/282 600/397 |
| 4,570,637 | A * | 2/1986 | Gomes | A61B 5/25 607/153 |
| 4,583,548 | A * | 4/1986 | Schmid | A61B 5/25 600/396 |
| 5,003,978 | A * | 4/1991 | Dunseath, Jr. | A61B 5/411 600/391 |
| 6,191,192 | B1 * | 2/2001 | Monden | C08K 5/0058 523/122 |
| 2002/0177767 | A1 * | 11/2002 | Burton | A61B 5/25 600/397 |
| 2010/0023404 | A1 | 1/2010 | Elgort et al. | |
| 2017/0135596 | A1 * | 5/2017 | Fan | A61B 5/291 |
| 2018/0116546 | A1 | 5/2018 | Pastoor et al. | |
| 2018/0235500 | A1 * | 8/2018 | Lee | H01B 13/0036 |
| 2018/0353096 | A1 * | 12/2018 | Mercier | A61B 5/6835 |
| 2022/0233124 | A1 * | 7/2022 | Connor | G06F 3/017 |

FOREIGN PATENT DOCUMENTS

| | | |
|---|---|---|
| JP | H11-206873 A | 8/1999 |
| WO | 2018-008688 A1 | 1/2018 |
| WO | WO 2018/008688 * | 1/2018 |

OTHER PUBLICATIONS

S. Takeda, "Special Feature: Latest Trend of Various Sensors for Measuring Biological Signals: The Technology on Electrode for Various Vital Potential", The Japanese Journal of Medical Instrumentation, vol. 80, No. 1, pp. 28-37 (2010).

N. Hoshimiya, "Important Factors of the Bioelectrodes", Japanese Journal of Electrocardiology vol. 4, No. 1, pp. 3-10 (1984).

T. Matsuo, "Properties of Recording Electrodes Connected through the Input Impedance of Bioelectronic Amplifier", Japanese Journal of Medical Electronics and Biological Engineering, vol. 8, No. 5, pp. 11-16, (1970).

International Search Report and Written Opinion for Application No. PCT/JP2019/022455 dated Aug. 20, 2019, with English Translation of the Search Report (10 pages).

Notice of Reasons for Refusal for corresponding Japanese application No. 2020-525491 dated Jun. 28, 2021 with English translation (10 Pages).

Gao et al., "Investigation on Permeation Properties of Liquids Into HTV Silicone Rubber Materials", IEEE Transactions on Dielectrics and Electrical Insulation, IEEE Service Center, Piscataway, NJ, US, vol. 21, No. 6, Dec. 1, 2014, pp. 2428-2437.

Extended European Search Report for corresponding Application No. 19819431.8 dated Feb. 3, 2022 (8 Pages).

First Chinese Office Action for corresponding Patent Application No. CN 20198005174.8 dated May 7, 2022 including English translation (15 pages).

International Preliminary Report on Patentability for corresponding International Application No. PCT/JP2019/022455 dated Dec. 15, 2020, with English translation of Written Opinion of the International Search Authority (10 pages).

Second Office Action issued in corresponding Chinese Application No. 201980005174.8 dated Nov. 21, 2022, with English translation (12 Pages).

Notification of the Rejection Decision for corresponding Chinese Patent Application No. CN 20198005174.8 dated Feb. 8, 2023, with English translation (11 pages).

* cited by examiner

METHOD FOR PRODUCING BIOELECTRODE

CROSS REFERENCE TO RELATED APPLICATIONS

The present application is a continuation application of International Patent Application No. PCT/JP2019/022455 filed on Jun. 6, 2019, which claims priority to Japanese Patent Application No. 2018-114504, filed on Jun. 15, 2018. The contents of the above applications are incorporated herein by reference in their entirety.

BACKGROUND

Technical Field

The present disclosure relates to a method for producing a bioelectrode.

Related Art

Sheets of highly electrically conductive metals such as gold, silver, platinum, and copper have been conventionally used as materials for bioelectrodes. These materials for bioelectrodes made of highly electrically conductive metals have poor adhesion to the skin, and detection of electrical signals from the skin is insufficient. Then, when these materials for bioelectrodes made of highly conductive metals are used, it is necessary to apply a gel, cream, paste, or the like to the skin in order to improve detection of electrical signals from the skin. Additionally, the materials for bioelectrodes made of highly electrically conductive metals, which are rigid, are not suitable to adhere to the skin for a long period. Then, in order to make adhesion with the skin for a long period easier, a bioelectrode composed of an adhesive material such as a gel has been suggested (see the Japanese journal of medical instrumentation, Vol. 80, No. 1 (2010) P28-37). In the bioelectrode described in the Japanese journal of medical instrumentation, Vol. 80, No. 1 (2010) P28-37, the adhesion to the skin is improved by use of an adhesive material without necessity of application of a gel, cream, paste, or the like.

Additionally, a bioelectrode has been suggested in which an electrically conductive silver coating layer containing a liquid silicone rubber and particles of silver is provided on a carbon-based electrically conductive silicone rubber surface and the silver coating layer is made to be a contact face to the skin (see International Publication No. WO 2018/008688). The bioelectrode described in International Publication No. WO 2018/008688, which is an electrode in which a rubber material is used in the silver coating layer, can be repetitively used, and additionally, the adhesion to the skin becomes satisfactory by means of the silver coating layer having flexibility. Additionally, the bioelectrode described in International Publication No. WO 2018/008688 has a two-layer structure of the carbon-based electrically conductive silicone rubber and the electrically conductive silver coating layer, and thus, high electrical conductivity is exhibited. Furthermore, since the contact face to the skin is the electrically conductive silver coating layer, the electrical conductivity becomes satisfactory, the contact impedance is low, and additionally, stable measurement can be achieved also under dry conditions where a paste or the like is not used. As mentioned above, what forms the majority of the bioelectrode of International Publication No. WO 2018/008688 is the carbon-based electrically conductive silicone rubber, and silver having electrical conductivity is used only in the silver coating layer. For this reason, the flexibility of the electrode is ensured as well as the amount of silver used is small. Thus, the production cost can be suppressed low.

In bioelectrodes, use of silver chloride can be contemplated in order to suppress a variation in the polarization voltage. With silver chloride, chloride ions serve as carriers to perform electrical conduction between the electrode and a living body. Thus, it is expected that the ions are unlikely to accumulate on the bioelectrode surface to thereby lower the variation in the polarization voltage.

However, the bioelectrode described in the Japanese journal of medical instrumentation, Vol. 80, No. 1 (2010) P28-37 has more satisfactory adhesion to the skin by means of the adhesive material without necessity of application of a gel, cream, paste, or the like, whereas trash and dust are likely to adhere to the adhesive material, and the adherence is gradually lost. Thus, the bioelectrode cannot be sufficiently repetitively used in some cases.

The bioelectrode described in International Publication No. WO 2018/008688 is a rubber electrode and can be repetitively used, whereas an electric double layer is formed at an interface between the skin and the bioelectrode during ionization of a silver powder as a filler and a polarization voltage may be generated. For this reason, the bioelectrode described in International Publication No. WO 2018/008688 has left room for further improvement in measurement of desired signals, from the viewpoint of a variation in the polarization voltage and a potential variation noise resulting therefrom.

Additionally, lowering the variation in the polarization voltage can be expected by use of silver chloride particles. However, silver chloride particles are likely to aggregate due to moisture absorption and require pulverization before use. Classification is also required in order to remove large particles in the silver chloride particles, and thus handling thereof is cumbersome. Silver chloride after pulverization and classification re-aggregates upon storage, and thus, pulverization and classification are performed on each amount to be used, which is cumbersome. Furthermore, silver chloride is highly corrosive. Thus, it is not possible to use common metal members for pulverization and classification of silver chloride, and a special treatment apparatus is required. Moreover, silver chloride particles are degraded by light. It is thus necessary to treat the silver chloride particles such that the particles are not exposed to light to a feasible extent, and thus, the operation becomes cumbersome.

Thus, a method also has been considered in which a sheet electrode containing a silver powder and a silicone rubber is produced in advance, and then, the sheet electrode is immersed in a sodium chloride aqueous solution to chlorinate the silver powder in the sheet electrode into silver chloride. However, in this method, the driving force in the case where chloride ions, which are provided by ionization in the aqueous solution, penetrate into the silicone rubber of the sheet electrode is natural diffusion. For this reason, further improvement on the penetrability of chloride ions into the sheet electrode is desired.

The present disclosure has been made in the view of such a situation, and is intended to provide a method for producing a bioelectrode capable of reducing potential variation noise due to a polarization voltage.

SUMMARY

The main features of the present disclosure are as follows.
(1) A method for producing a bioelectrode including:

forming an electrically conductive rubber body containing a silicone rubber and a silver powder; and immersing the electrically conductive rubber body in an inorganic salt-containing solution at 70° C. or more and 180° C. or less.

(2) The method for producing a bioelectrode according to the above (1), wherein the inorganic salt-containing solution contains at least one inorganic salt selected from the group consisting of sodium chloride, potassium chloride, lithium chloride, calcium chloride, magnesium chloride, sodium sulfate, potassium sulfate, lithium sulfate, calcium sulfate, magnesium sulfate, sodium carbonate, potassium carbonate, lithium carbonate, calcium carbonate, and magnesium carbonate.

(3) The method for producing a bioelectrode according to the above (1), wherein, in immersing the electrically conductive rubber body in the inorganic salt-containing solution, the electrically conductive rubber body is immersed in the inorganic salt-containing solution under a pressure of 1 atm or more and 10 atm or less.

(4) The method for producing a bioelectrode according to the above (1), wherein, in forming the electrically conductive rubber body, an electrically conductive rubber body having a layered shape is formed.

(5) The method for producing a bioelectrode according to the above (1), wherein, in forming the electrically conductive rubber body, an electrically conductive rubber body having a brush-like shape is formed.

It is possible to provide a method for producing a bioelectrode capable of reducing potential variation noise due to a polarization voltage.

DETAILED DESCRIPTION

Bioelectrode

A bioelectrode obtained by a method for producing a bioelectrode according to an embodiment of the present disclosure has, as required, an electrically conductive substrate, and an electrically conductive rubber body containing a silicone rubber, a silver powder, and an inorganic salt. When the bioelectrode has an electrically conductive substrate, the bioelectrode has the electrically conductive rubber body on the electrically conductive substrate. The silicone rubber contained in the electrically conductive rubber body has active mobility of the molecular chains, and thus, molecules, atoms, ions, and the like are more likely to penetrate by dissolution and diffusion into the molecular chains than into other polymers. Then, an inorganic salt and anions and cations derived from the inorganic salt have penetrated into the molecular chains. Potential variation noise due to the polarization voltage of silver ions can be reduced by the inorganic salt, anions, cations, and the like. It is also possible to solve problems based on a pulverization treatment and corrosion of silver chloride as in the case where silver chloride is used as a material for the electrically conductive rubber body. The shape of the electrically conductive rubber body forming the bioelectrode is not particularly limited, and the electrically conductive rubber body may take any desired shape such as a layered, brush-like, and recessed and protruding shape, depending on the type and surface profile of a measurement target.

Hereinafter, a bioelectrode obtained by a production method of the embodiment of the present disclosure will be described with reference to the accompanying drawings. Note that the present disclosure is not limited by the following embodiments in any way.

Figure 1:
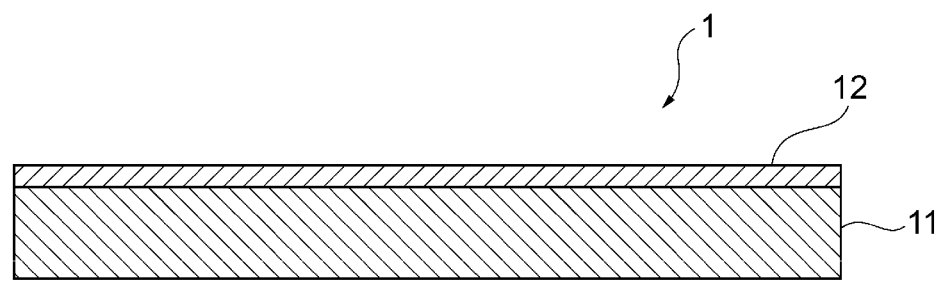
FIG. 1 is a schematic cross-sectional view illustrating one example of a bioelectrode obtained by a method for producing a bioelectrode according to an embodiment of the present disclosure.

FIG. 1 is a schematic cross-sectional view illustrating one example of a bioelectrode 1 obtained by a production method according to the present embodiment. The bioelectrode 1 according to the present embodiment is suitably used for at least either one of sensing of electrical signals from a living body or transmission of electrical stimuli to a living body. As shown in FIG. 1, the bioelectrode 1 includes an electrically conductive substrate 11 including an electrically conductive silicone rubber and an electrically conductive rubber body 12 provided on the electrically conductive substrate 11. In the example of FIG. 1, the electrically conductive rubber body 12 has a layered shape. In other words, in the bioelectrode 1, the electrically conductive rubber body 12 is provided as an electrically conductive rubber layer covering the electrically conductive substrate 11 containing the electrically conductive silicone rubber. This can further improve the adhesion of the electrically conductive rubber body 12 to a living body.

Figure 2:
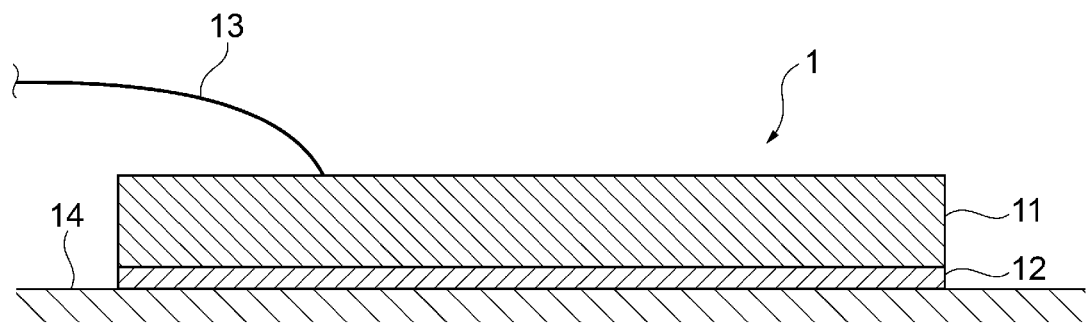
FIG. 2 is an explanatory view illustrating a usage state of a bioelectrode obtained by the method for producing a bioelectrode according to the embodiment of the present disclosure.

FIG. 2 is an explanatory view illustrating a usage state of the bioelectrode 1 according to the present embodiment. As shown in FIG. 2, the bioelectrode 1 causes the surface of the electrically conductive rubber body 12 to contact a living body 14, for example, while connecting a signal transmission member 13, which is connected to a measuring apparatus (not shown), to the surface of the electrically conductive substrate 11. This causes electrical signals from the living body 14 to be transmitted, via the electrically conductive rubber body 12, the electrically conductive substrate 11, and the signal transmission member 13, to the measuring apparatus, and thus, the electrical signals from the living body 14 can be measured. The bioelectrode 1 is directly contacted to a living body and used. Thus, the electrically conductive rubber body 12 has a predetermined contact area (outermost surface area). The area of the electrically conductive rubber body 12 contacting with a living body is preferably 0.2 cm$^2$ or more and 13 cm$^2$ or less, more preferably 1 cm$^2$ or more and 8 cm$^2$ or less, still more preferably 3 cm$^2$ or more and 7 cm$^2$ or less. When the contact area of the electrically conductive rubber body 12 is within the above range, it is possible to effectively prevent mixing of noise by lowering the impedance. Additionally, the measurement results are not subjected to influence of body movements, and it is possible to contact the bioelectrode 1 to a small area of a living body.

Figure 3A:
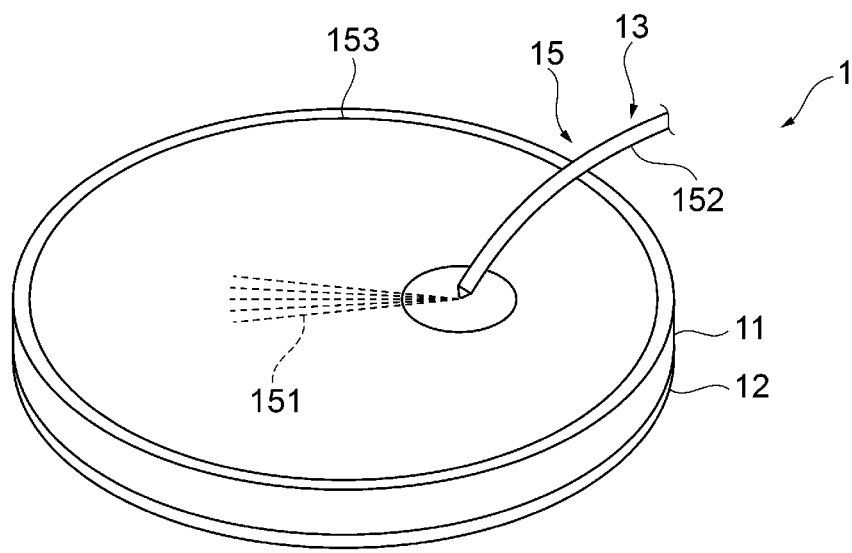
FIG. 3A is an explanatory view of a signal transmission member of the bioelectrode obtained by the method for producing a bioelectrode according to the embodiment of the present disclosure.
Figure 3B:
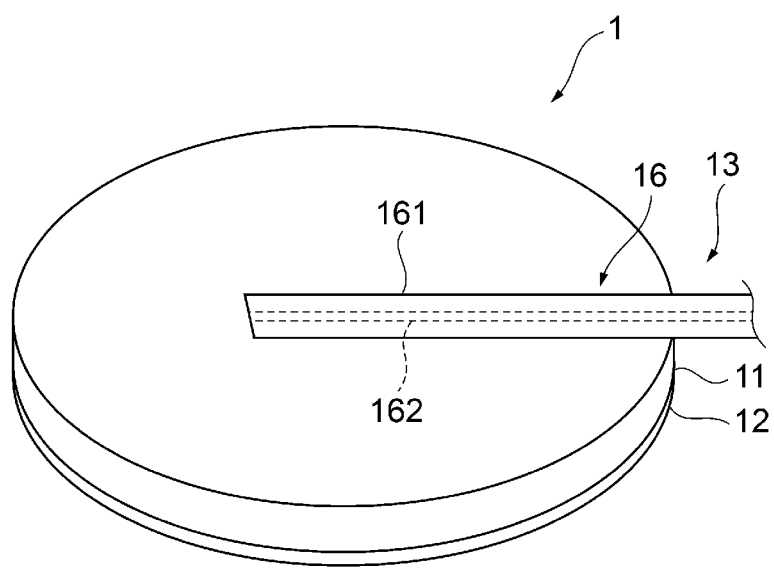
FIG. 3B is an explanatory view of another example of the signal transmission member of the bioelectrode obtained by the method for producing a bioelectrode according to the embodiment of the present disclosure.

FIG. 3A and FIG. 3B are explanatory views of the signal transmission member 13 of the bioelectrode 1 obtained by the production method according to the present embodiment. The example shown in FIG. 3A illustrates an example in which a coated wire 15 is used as the signal transmission member 13. The coated wire 15 includes a core wire 151 made of metal having electrical conductivity and a coating material 152 made of a resin with which the core wire 151 is coated. In this coated wire 15, the tip end portion of the core wire 151 is exposed from the coating material 152. The exposed tip end portion of the core wire 151 is fixed on the surface of the electrically conductive substrate 11 with adhesive tape 153 or the like. With such a configuration, electrical signals flowing across the electrically conductive substrate 11 are transmitted externally by the coated wire 15 via the core wire 151, and thus, electrical signals from the living body 14 can be transmitted externally.

The example shown in FIG. 3B illustrates an example in which a flexible printed board 16 is used as the signal transmission member 13. The flexible printed board 16 includes a base film made of a resin 161 and a conductor foil 162 made of a metal provided on the base film 161. The conductor foil 162 is copper or copper plated with gold. With such a configuration, electrical signals flowing across the electrically conductive substrate 11 are transmitted externally by the flexible printed board 16 via the conductor foil 162, and thus, electrical signals from the living body 14 can be transmitted externally.

In the example shown in FIG. 3A, the coated wire 15 having a predetermined thickness, as the signal transmission member 13, is disposed on the upper face side of the electrically conductive substrate 11. For this reason, when the bioelectrode 1 is fitted to the living body 14, an uneven load due to the thickness of the coated wire 15 is applied to the electrically conductive rubber body 12, which directly contacts the living body 14 (see FIG. 2, the same applies to hereinafter), and unevenness may be felt at the fitting portion of the living body 14. In contrast, in the example shown in FIG. 3B, the surface of the plate-like flexible printed board 16, as the signal transmission member 13, is substantially coplanar with the surface of the electrically conductive substrate 11. This makes a load due to the thickness of the flexible printed board 16 unlikely to be applied to the electrically conductive rubber body 12. For this reason, unevenness is unlikely to be felt at fitting part even the bioelectrode 1 is fitted for a long time, and discomfort can be reduced. Simultaneously, the downsizing and lighter weight of bioelectrode 1 can be achieved.

Figure 4:
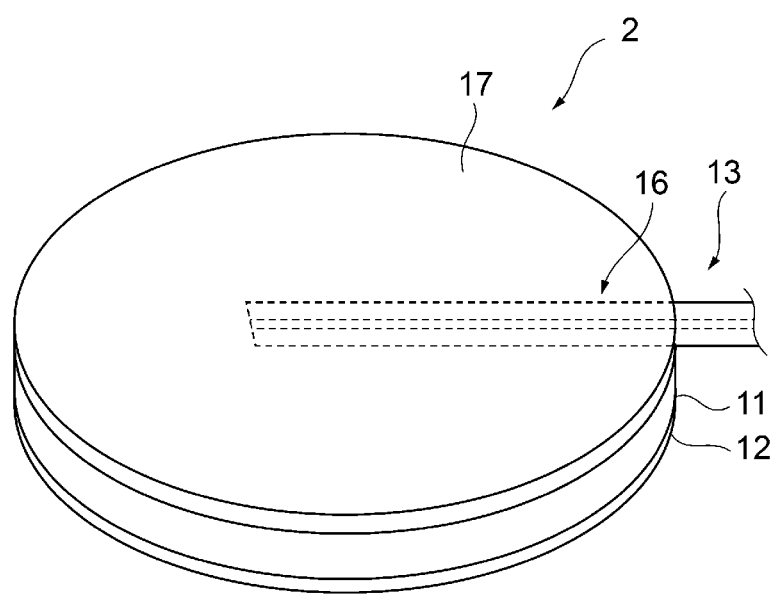
FIG. 4 is a view illustrating another configuration example of the bioelectrode obtained by the method for producing a bioelectrode according to the embodiment of the present disclosure.

FIG. 4 is a view illustrating another example of the bioelectrode 1 obtained by the production method according to the present embodiment. In the example shown in FIG. 4, a bioelectrode 2 includes an insulation layer 17 provided on an electrically conductive substrate 11. The insulation layer 17 contains an insulating rubber. In the bioelectrode 2, when the insulation layer 17 is provided on the electrically conductive substrate 11, the surface of the electrically conductive substrate 11 does not directly contact the living body 14. Thus, transmission of electrical signals from the living body 14 is not impeded by the insulation layer 17. Then, in the case where the insulation layer 17 is provided, the surface of the flexible printed board 16 becomes substantially coplanar with the surface of the electrically conductive substrate 11 by providing the flexible printed board 16 as the signal transmission member 13, as shown in FIG. 3B. For this reason, the insulation layer 17 can be stably maintained as well as bending of the bioelectrode 2 can be prevented.

Hereinafter, each component of the bioelectrode will be described in detail.

The material for the electrically conductive substrate 11 is not particularly limited as long as the material has electrical conductivity. For example, an electrically conductive silicone rubber including a silicone rubber and electrical conductivity particles can be used. The electrically conductive substrate 11 can improve adhesion between the electrically conductive substrate 11 and the electrically conductive rubber body 12 by containing the electrically conductive silicone rubber. As the silicone rubber, a liquid silicone rubber is preferable. For example, an organosilicon polymer can be used. As the organosilicon polymer, preferable is one having a siloxane bond (—Si—O—) as the main chain and having a hydrocarbon group such as a methyl group, a phenyl group, or a vinyl group or hydrogen as a side chain. As the silicone rubber, an addition-reactive silicone rubber may be used, or a condensation-reactive silicone rubber may be used. The addition-reactive silicone rubber is a silicone rubber to be cured by an addition reaction, and examples thereof include silicone rubbers having hydrogen or a vinyl group as a side chain. The condensation-reactive silicone rubber is a silicone rubber to be cured by a condensation reaction, and examples thereof include silicone rubbers having a hydroxyl group at its terminal. Among these, the addition-reactive silicone rubber is preferable, from the viewpoint that the adhesion with the electrically conductive rubber body 12 is more suitably maintained. One of these silicone rubbers may be used singly, or two or more of these may be used in combination.

As the electrical conductivity particles, electrically conductive carbon particles such as various carbon blacks are used. The electrically conductive carbon particles are not limited as long as the particles can impart electrical conductivity to the electrically conductive substrate 11. Examples of the electrically conductive carbon particles include various carbon particles such as carbon black and graphite. Examples of the carbon black include Ketjen black and acetylene black. One of these may be used singly, or two or more of these may be used in combination. Among these, as carbon black, Ketjen black is preferable, from the viewpoint of improving the electrical conductivity of the electrically conductive substrate 11.

The average particle size of the electrically conductive particles is not particularly limited as long as the average particle size is within a range where electrical conductivity can be imparted to the electrically conductive substrate 11. The average particle size of the electrically conductive particles is preferably 0.1 μm or more and 100 μm or less, more preferably 1 μm or more and 30 μm or less, from the viewpoint of improving the electrical conductivity of the electrically conductive substrate 11 and the viewpoint of attaining the flexibility of the electrically conductive substrate 11. The average particle size of the electrically conductive particles is an average diameter determined by measurement of an electron micrograph and calculation using the arithmetic mean.

The content of the electrically conductive particles in the electrically conductive substrate 11 is not particularly limited as long as the content is within a range where electrical conductivity can be imparted to the electrically conductive substrate 11. The content of the electrically conductive particles in the electrically conductive substrate 11 is preferably 10% by mass or more and 70% by mass or less, more preferably 20% by mass or more and 50% by mass or less based on the total mass of the electrically conductive substrate 11, from the viewpoint of improving the electrical conductivity of the electrically conductive substrate 11 and the viewpoint of attaining the flexibility of the electrically conductive substrate 11.

As the electrically conductive silicone rubber contained in the electrically conductive substrate 11, a commercially available product may be used, for example, trade name "KE-3801M-U" (manufactured by Shin-Etsu Chemical Co., Ltd.).

Alternatively, the electrically conductive substrate 11 can be one obtained by crosslinking the electrically conductive silicone rubber mentioned above by a crosslinking agent. As the crosslinking agent, a commercially available product may be used, for example, trade name "C-8A" (2,5-dimethyl-2,5-bis(t-butylperoxy)hexane content: 80% by weight, manufactured by Shin-Etsu Chemical Co., Ltd.).

The thickness of the electrically conductive substrate 11 is not particularly limited as long as the thickness is within a range where the flexibility of the electrically conductive substrate 11 can be attained, and is preferably 0.1 mm or more and 2 mm or less, more preferably 0.4 mm or more and 1.5 mm or less.

The electrically conductive rubber body 12 contains a silicone rubber, a silver powder, an inorganic salt, and additives such as a dispersant as required. As the silicone rubber included in the electrically conductive rubber body 12, one similar to a silicone rubber to be used in the electrically conductive substrate 11 mentioned above can be used, and a liquid silicone rubber is preferably used. Also as the silicone rubber, a silicone rubber in which a predetermined amount of a curing agent is compounded may be used. Examples of the silicone rubber include trade name "KE-106" (silicone rubber: manufactured by Shin-Etsu Chemical Co., Ltd.) and "CAT-RG" (curing agent: manufactured by Shin-Etsu Chemical Co., Ltd.).

The electrically conductive rubber body 12 contains 50 to 600 parts by mass of, preferably 100 to 400 parts by mass of the silver powder based on 100 parts by mass of the silicone rubber, from the viewpoint of improving the electrical conductivity.

As the silver powder to be included in the electrically conductive rubber body 12, for example, an aggregated silver powder and a flaky silver powder can be used. One of these silver powders may be used singly, or two or more of these may be used in combination.

The flaky silver powder is a silver powder having a scale-like shape. Examples of the flaky silver powder include trade name "327077" (manufactured by Sigma-Aldrich Co. LLC.), trade name "FA-D-3" (manufactured by DOWA Electronics Materials Co., Ltd.), and trade name "FA-2-3" (manufactured by DOWA Electronics Materials Co., Ltd.).

The aggregated silver powder is a silver powder of a plurality of particulate primary particles three-dimensionally aggregated. An example of the aggregated silver powder is trade name "G-35" (manufactured by DOWA Electronics Materials Co., Ltd.).

The average particle size of the silver powder is not particularly limited as long as the average particle size is within a range where electrical conductivity can be imparted to the electrically conductive rubber body 12. The average particle size of the aggregated silver powder is preferably 4 μm or more and 8 μm or less. The average particle size of the flaky silver powder is preferably 5 μm or more and 15 μm or less. Note that the average particle size of the silver powder is an average diameter determined by measurement of an electron micrograph and calculation using the arithmetic mean.

As the silver powder, an aggregated first silver powder and a flaky second silver powder can be used in combination, from the viewpoint of improving the electrical conductivity of the electrically conductive rubber body 12. When the first silver powder and the second silver powder are used in combination, the mass ratio between the content of the first silver powder and the content of the second silver powder (first silver powder:second silver powder) is preferably 1:3 to 3:1.

The inorganic salt is not particularly limited as long as the inorganic salt can penetrate into the electrically conductive rubber body 12, and at least one inorganic salt selected from the group consisting of chloride salts, sulfates, and carbonates is preferably used. As the inorganic salt, at least one inorganic salt selected from the group consisting of sodium chloride, potassium chloride, lithium chloride, calcium chloride, magnesium chloride, sodium sulfate, potassium sulfate, lithium sulfate, calcium sulfate, magnesium sulfate, sodium carbonate, potassium carbonate, lithium carbonate, calcium carbonate, and magnesium carbonate is more preferably used. One of these inorganic salts may be used singly, or two or more of these may be used in combination. Among these, the inorganic salt is preferably a chloride salt, more preferably a chloride salt of an alkali metal such as sodium chloride, potassium chloride, and lithium chloride, from the viewpoint of solubility in a solvent and ion mobility. Additionally, as the inorganic salt, sodium chloride is even more preferable, from the viewpoint of its low costs, safety to the human body, and ion exchangeability with salt contained in perspiration of the human body. Furthermore, the electrically conductive rubber body 12 can contain, as anions derived from the inorganic salt, halide ions, sulfate ions, and carbonate ions. As the halide ions, chloride ions (Cl$^-$) are preferable. The electrically conductive rubber body 12 can contain, as cations derived from the inorganic salt, Li$^+$, Na$^+$, K$^+$, Mg$^{2+}$, Ca$^{2+}$, or the like, but Na$^+$ is preferable because Na$^+$ has the lowest influence on the human body. Such an inorganic salt and anions and cations derived from the inorganic salt penetrate into the electrically conductive rubber body 12 to suppress a potential variation due to the polarization voltage in the electrically conductive rubber body 12 and enable potential variation noise to be effectively reduced.

The inorganic salt and anions and cations derived from the inorganic salt may be homogeneously distributed in the electrically conductive rubber body 12 or may be distributed toward the thickness direction of the electrically conductive rubber body 12 so as to have a concentration gradient. Note that, in the case where the inorganic salt and anions and cations derived from the inorganic salt are distributed toward the thickness direction of the electrically conductive rubber body 12 so as to have a concentration gradient, the inorganic salt and anions and cations derived from the inorganic salt can be distributed such that the concentration is higher on the surface side of the electrically conductive rubber body 12 and the concentration is lower on the electrically conductive substrate side.

The electrically conductive rubber body 12 may further contain a modified silicone as a dispersant. As the modified silicone, ones obtained by introducing a side chain that causes modification to the main chain formed of a siloxane bond (—Si—O—; also referred to as a silicone chain) can be preferable used. Examples thereof include silicones containing polyether modification, polyether-alkyl commodification, polyglycerin modification, polyglycerin-alkyl commodification, or the like. The side chain that causes modification preferably contains an ether bond (—C—O—C—).

As the polyether-modified silicone, ones obtained by introducing a side chain formed of a polyether chain into the main chain formed of a silicone chain can be used.

As the polyether-alkyl-commodified silicone, ones obtained by introducing a side chain formed of a polyether chain and a side chain formed of an alkyl chain into the main chain formed of a silicone chain can be used.

As the polyglycerin-modified silicone, ones obtained by introducing a side chain formed of a polyglycerin chain into the main chain formed of a silicone chain can be used.

As the polyglycerin-alkyl-commodified silicone, ones obtained by introducing a side chain formed of a polyglycerin chain and a side chain formed of an alkyl chain into the main chain formed of a silicone chain can be used.

Among these, the polyether-modified silicone and the polyglycerin-modified silicone are particularly preferable.

Optionally, the modified silicone can also function as an electrical conductivity improving material for the electrically conductive rubber body 12. In this case, the modified silicone suitably can function as an electrical conductivity improving material that forms a path for migration of the anions and cations derived from the inorganic salt to thereby facilitate ion conduction. As a result of this, it is possible to maintain the electrical conductivity of the bioelectrode for a long period.

The thickness of the electrically conductive rubber body 12 is not particularly limited as long as the thickness is within a range where electrical conductivity can be imparted to the electrically conductive rubber body 12. The thickness of the electrically conductive rubber body 12 is preferably 18 µm or more and 80 µm or less, from the viewpoint of improving the electrical conductivity of the bioelectrode and the viewpoint of attaining the flexibility of the bioelectrode. Additionally, the thickness of the electrically conductive rubber body 12 is more preferably 30 µm or more and 60 µm or less, from the viewpoint of improving the adhesion between the electrically conductive substrate 11 and the electrically conductive rubber body 12 to prevent delamination of the electrically conductive rubber body 12 as well as reducing the contact impedance with a living body.

Figure 5:
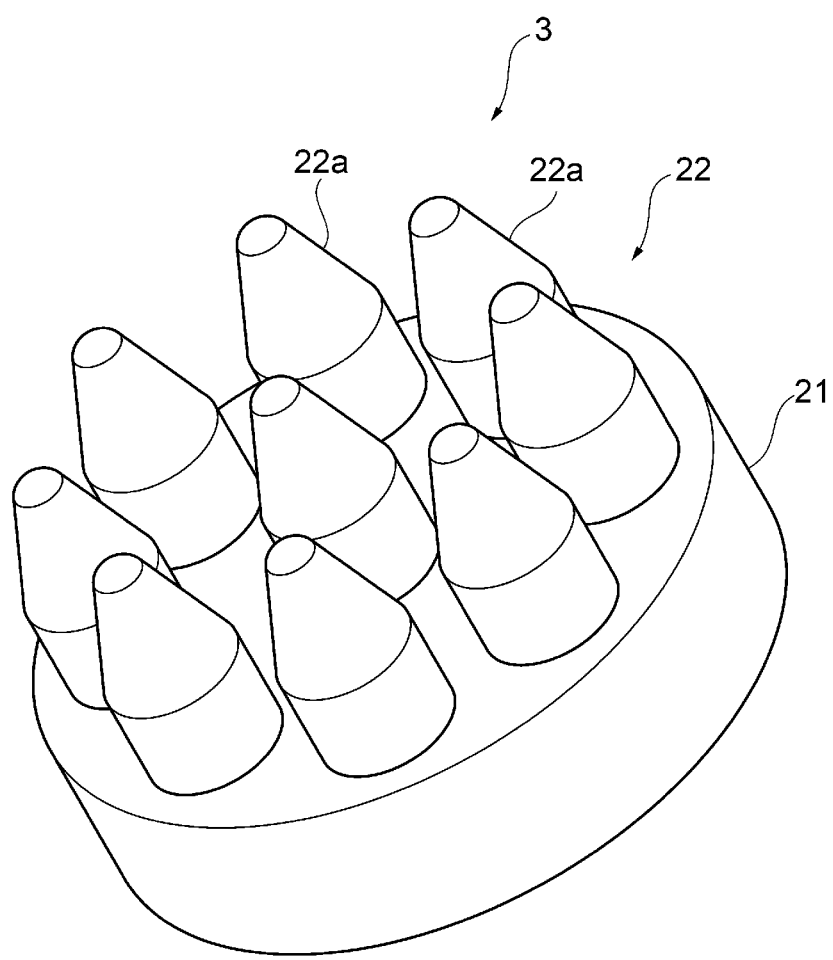
FIG. 5 is a perspective view illustrating another example of the bioelectrode obtained by the method for producing a bioelectrode according to the embodiment of the present disclosure.
Figure 6:
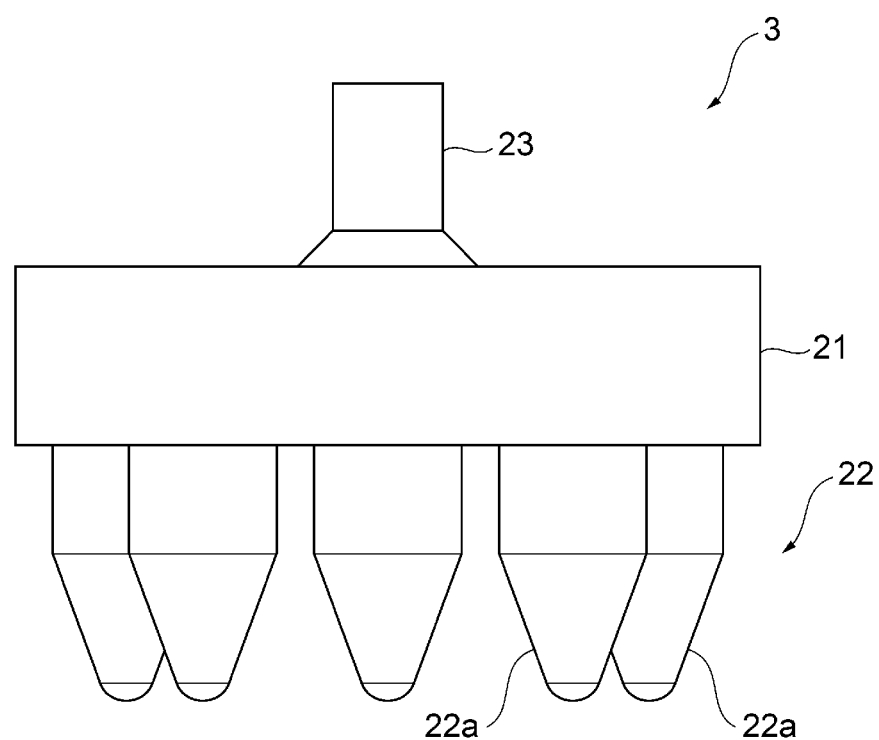
FIG. 6 is a cross-sectional view illustrating another example of the bioelectrode obtained by the method for producing a bioelectrode according to the embodiment of the present disclosure.
Figure 7:
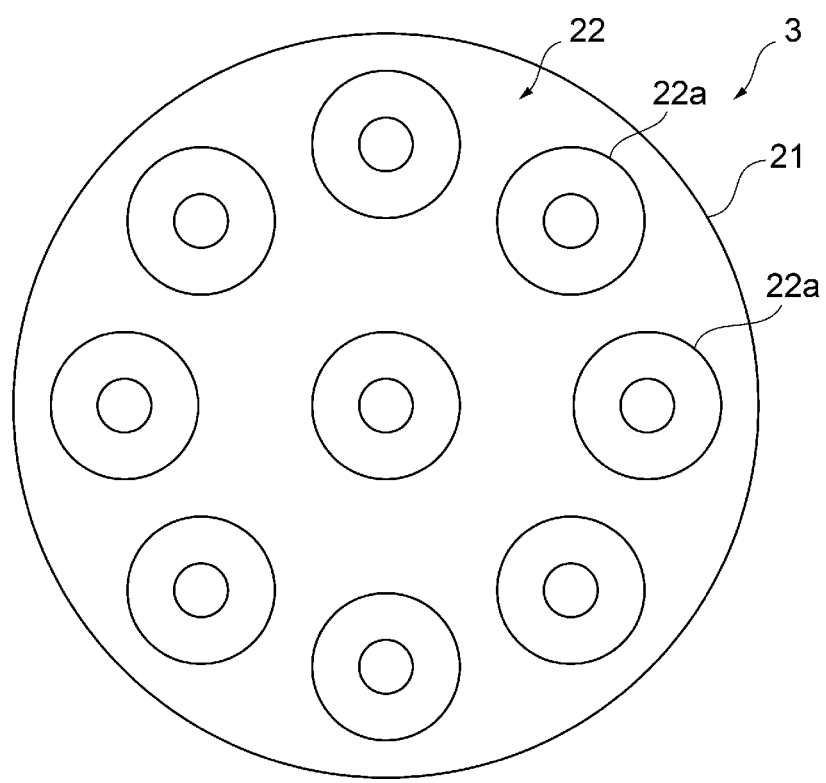
FIG. 7 is a top view illustrating another example of the bioelectrode obtained by the method for producing a bioelectrode according to the embodiment of the present disclosure.
Figure 8:
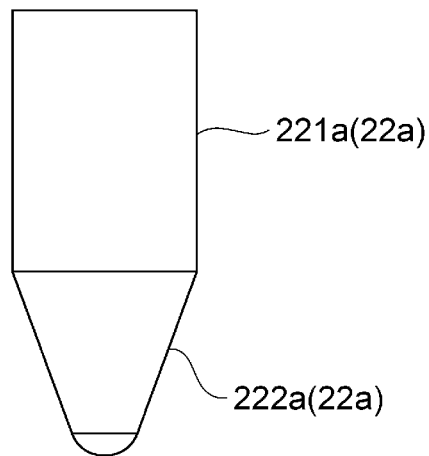
FIG. 8 is a partial side view of another example of the bioelectrode obtained by the method for producing a bioelectrode according to the embodiment of the present disclosure.

FIGS. 5 to 8 are views illustrating another example of the bioelectrode obtained by the production method according to the present embodiment. Note that FIG. 5 is a perspective view of a bioelectrode 3, FIG. 6 is a side view of the bioelectrode 3, FIG. 7 is a top view of the bioelectrode 3, and FIG. 8 is a partial side view illustrating only a projection body 22a forming the bioelectrode 3.

As shown in FIG. 5 to FIG. 7, the bioelectrode 3 is formed of an electrically conductive rubber body comprising a disk 21 and a projection portion 22 provided on one face of the disk 21. The projection portion 22 has a brush-like shape formed of a plurality of projection bodies 22a. The projection portion 22 is formed of a projection body 22a disposed on the center of the disk 21 and a plurality of projection bodies 22a disposed on the circumference centered on the projection body 22a. On the other main face of the disk 21, a connection member 23 is provided.

As shown in FIG. 8, the projection body 22a includes a main body portion 221a and a tip end portion 222a provided on the main body portion 221a. The main body portion 221a has a substantially cylindrical shape, of which one end side is provided on the disk 21. The tip end portion 222a has a substantially conical shape, of which apex side has a hemispherical shape. The bottom face of the tip end portion 222a is provided on the surface of another end side of the main body portion 221a.

In the bioelectrode 3 illustrated in FIGS. 5 to 8, a plurality of projection bodies 22a serve as a brush-shaped terminal and contacts a human body. Meanwhile, no discomfort occurs during contact with the skin because the apex side of the tip end portion 222a of each projection body 22a has a hemispherical shape, and the adhesion with the skin becomes satisfactory because of the flexibility of the projection body 22a. Additionally, the face to contact the skin has electrical conductivity due to silver, and thus, the contact impedance is low. Stable measurement can be achieved also under dry conditions where a paste or the like is not used. The present embodiment is also applicable to the bioelectrode 3 comprising an electrically conductive rubber body 22 having such a brush-shaped terminal.

Method for Producing Bioelectrode

The method for producing a bioelectrode according to the embodiment of the present disclosure has forming an electrically conductive rubber body containing a silicone rubber and a silver powder and immersing the electrically conductive rubber body in an inorganic salt-containing solution at 70° C. or more and 180° C. or less. The silicone rubber contained in the electrically conductive rubber body usually has active mobility of the molecular chains, and thus, molecules, atoms, ions, and the like are more likely to penetrate by dissolution and diffusion into the molecular chains than into other polymers. Additionally, in the present embodiment, the inorganic salt-containing solution is at a high temperature of 70° C. or more and 180° C. or less. Thus, movements of the molecular chains of the silicone rubber become more active in the inorganic salt-containing solution, and the migration velocity of an inorganic salt, anions, and cations in the electrically conductive rubber body can be enhanced. This enables the inorganic salt and anions and cations derived from the inorganic salt to penetrate into the electrically conductive rubber body more rapidly in a larger amount than in the case at normal temperature (e.g., room temperature, 25° C.). As a result of this, the potential variation due to the polarization voltage in the electrically conductive rubber body is suppressed by the inorganic salt and anions and cations derived from the inorganic salt to thereby enable potential variation noise to be reduced. Additionally, in one example, the inorganic salt is dissolved in the inorganic salt-containing solution in which the electrically conductive rubber body is to be immersed, and thus, the inorganic salt and anions and cations derived from the inorganic salt can efficiently act on suppression of the polarization voltage.

In forming an electrically conductive rubber body, (a) the electrically conductive rubber body may be formed on an electrically conductive substrate, or (b) the electrically conductive rubber body may be formed singly. In the case where the electrically conductive rubber body is formed on an electrically conductive substrate, for example, a method can be exemplified in which a silver paste containing a liquid silicone rubber, a silver powder, and as required, a crosslinking agent, a modified silicone, and the like is applied on an electrically conductive substrate, and then, the silver paste is cured by heating. In the case where the electrically conductive rubber body is formed singly, a method can be exemplified in which a silver paste is injected into a mold having a predetermined internal shape, and then, the silver paste is cured in the mold by heating. Typically, in the case of above (a), an layered electrically conductive rubber body can be formed on an electrically conductive substrate, and in the case of above (b), an electrically conductive rubber body having a desired shape such as a brush shape can be formed.

The inorganic salt-containing solution to be used in immersing the electrically conductive rubber body preferably contains an inorganic salt, a solvent to dissolve the inorganic salt, and other additives as required.

The inorganic salt to be contained in the inorganic salt-containing solution is not particularly limited as long as the inorganic salt can penetrate into the electrically conductive rubber body, but at least one inorganic salt selected from the group consisting of chloride salts, sulfates, and carbonates is preferably used. As the inorganic salt, at least one inorganic salt selected from the group consisting of sodium chloride, potassium chloride, lithium chloride, calcium chloride, magnesium chloride, sodium sulfate, potassium sulfate, lithium sulfate, calcium sulfate, magnesium sulfate, sodium carbonate, potassium carbonate, lithium carbonate, calcium carbonate, and magnesium carbonate is more preferably used. One of these inorganic salts may be used singly, or two or more of these may be used in combination. Among these, the inorganic salt is preferably a chloride salt, more preferably a chloride salt of an alkali metal such as sodium chloride, potassium chloride, and lithium chloride, from the viewpoint of solubility in a solvent and ion mobility. Sodium chloride is even more preferable, from the viewpoint of its low costs, safety to the human body, and ion exchangeability with salt contained in perspiration of the human body. Additionally, the electrically conductive rubber body can contain, as anions derived from the inorganic salt, halide ions, sulfate ions, and carbonate ions. As the halide ions, chloride ions ($Cl^-$) are preferable. The electrically conductive rubber body can contain, as cations derived from the inorganic salt, $Li^+$, $Na^+$, $K^+$, $Mg^{2+}$, $Ca^{2+}$, or the like. Such an inorganic salt and anions and cations derived from the inorganic salt penetrate into the electrically conductive rubber body to suppress a potential variation due to the polarization voltage in the electrically conductive rubber body and enable potential variation noise to be effectively reduced. The concentration of the inorganic salt in the inorganic salt-containing solution is preferably 0.1 mol/L or more, more preferably 0.5 mol/L or more and 20 mol/L or less. With the concentration of the inorganic salt in the inorganic salt-containing solution within these ranges, it is possible to allow the inorganic salt and anions and cations derived from the inorganic salt to effectively penetrate into the electrically conductive rubber body.

The solvent to be contained in the inorganic salt-containing solution is not particularly limited as long as the solvent can dissolve the inorganic salt. Examples of the solvent include water, ketones such as acetone, and alcohols such as ethanol and methanol. One of these solvents may be used singly, or two or more of these may be used in combination. Among these, water, ethanol, or a mixture of water and ethanol is preferable from the viewpoint of safety and low costs, and water is preferable from the viewpoint of safety and low costs.

In immersing the electrically conductive rubber body in an inorganic salt-containing solution, the temperature of the inorganic salt-containing solution is preferably 100° C. or more and 150° C. or less, more preferably 115° C. or more and 135° C. or less. With the temperature of the inorganic salt-containing solution within these ranges, it is possible to allow the inorganic salt and anions and cations derived from the inorganic salt to effectively penetrate into the electrically conductive rubber body without degrading the electrically conductive rubber body. As a result of this, it is possible to effectively reduce the potential variation noise due to the polarization voltage in the electrically conductive rubber body.

Hereinafter, the method for producing a bioelectrode of the present embodiment will be concretely described.

(a) In the case where the electrically conductive rubber body is formed on an electrically conductive substrate, first, an electrically conductive substrate is provided. The electrically conductive substrate may be one in which a commercially available material is used or may be one newly produced. In the case where an electrically conductive substrate is newly produced, for example, an electrically conductive silicone rubber containing electrically conductive particles and a crosslinking agent in a predetermined amount are kneaded with a kneading apparatus such as a kneader and a roll at room temperature (20° C. or more and 40° C. or less) for one minute or more and one hour or less to obtain a material. Thereafter, the kneaded material is primary-crosslinked under conditions of 100° C. or more and 300° C. or less and one minute or more and one hour or less. Then, an electrically conductive substrate is produced by conducting secondary crosslinking under conditions of 150° C. or more and 350° C. or less and one hour or more and 10 hours or less.

Thereafter, a silver paste is produced by stirring a liquid silicone rubber, a silver powder, a crosslinking agent, and the like with a mixer or the like for a predetermined time. The temperature during stirring may be, for example, room temperature (20° C. or more and 40° C. or less). The stirring time may be, for example, one minute or more and one hour or less. Thereafter, the silver paste is applied on the electrically conductive substrate. For application of the silver paste on the electrically conductive substrate, immersion, spraying, a roll coater, a flow coater, inkjet, screen printing, or the like is used, for example. The thickness of the silver paste applied is preferably 25 μm or more and 200 μm or less, more preferably 35 μm or more and 100 μm or less. This can enhance the adhesion of the electrically conductive rubber body to the electrically conductive substrate. Thus, delamination of the electrically conductive rubber body from the electrically conductive substrate is more likely to be prevented as well as the contact impedance can be lowered. Then, the silver paste is cured. In this step, the silver paste can be cured by heating the silver paste to a predetermined temperature for a predetermined time, for example. The heating time for the silver paste is preferably 10 to 120 minutes, more preferably 15 to 90 minutes, even more preferably 20 to 45 minutes. The heating temperature for the silver paste is preferably 100 to 200° C., more preferably 120 to 180° C., even more preferably 140 to 160° C. The silver paste can be cured by heating at 150° C. for 30 minutes, for example.

(b) In the case where an electrically conductive rubber body is formed singly, a silver paste is produced as in the above (a). Thereafter, the silver paste is injected into a mold corresponding to a desired shape such as a brush shape, and then, primary crosslinking by means of press crosslinking is conducted. Thereafter, secondary crosslinking is further conducted. Specifically, the kneaded material is primary-crosslinked under conditions of 100° C. or more and 300° C. or less and one minute or more and one hour or less. Then, an electrically conductive rubber body is produced by conducting secondary crosslinking under conditions of 150° C. or more and 350° C. or less and one hour or more and 10 hours or less.

After the electrically conductive rubber body is formed as in the above (a) or (b), the electrically conductive rubber body is immersed in an inorganic salt-containing solution at 70° C. or more and 180° C. or less. During immersion in the inorganic salt-containing solution, the inorganic salt and anions and cations derived from the inorganic salt effectively penetrate into the electrically conductive rubber body.

In immersing the electrically conductive rubber body in an inorganic salt-containing solution, the electrically conductive rubber body is preferably immersed in the inorganic salt-containing solution under a pressurized condition. The electrically conductive rubber body is immersed in the inorganic salt-containing solution more preferably under a pressure of 1 atm or more and 10 atm or less, even more preferably under a pressure of 2 atm or more and 3 atm or less. The penetration rate of the inorganic salt and anions and cations derived from the inorganic salt into the electrically conductive rubber body is enhanced by immersing the electrically conductive rubber body in the inorganic salt-containing solution under a pressurized condition to thereby enable the concentration of the inorganic salt, anions and cations in the electrically conductive rubber body to effectively increase. As a result of this, it is possible to effectively reduce the potential variation noise of the bioelectrode. The pressurization method is not particularly limited, and examples thereof can include a method in which the electrically conductive rubber body is placed in a sealed vessel (e.g., an autoclave) into which the inorganic salt-containing solution has been injected, and then, the pressure in the sealed vessel is raised.

The time for immersing the electrically conductive rubber body in the inorganic salt-containing solution can be appropriately changed in accordance with the temperature of the inorganic salt-containing solution, the inorganic salt concentration in the inorganic salt-containing solution, and the pressure during pressurization. The immersion time for the electrically conductive rubber body in the inorganic salt-containing solution is preferably 15 minutes or more and 180 minutes or less, more preferably 30 minutes or more and 120 minutes or less, even more preferably 45 minutes or more and 90 minutes or less, from the viewpoint of efficiently dispersing the inorganic salt and anions and cations derived from the inorganic salt in the electrically conductive rubber body.

As described hereinabove, according to the embodiment described above, a large amount of the inorganic salt and anions and cations derived from the inorganic salt present in the inorganic salt-containing solution rapidly penetrate into the electrically conductive rubber body by immersing the electrically conductive rubber body in the inorganic salt-containing solution at 70° C. or more and 180° C. or less. Note that this penetration process of the inorganic salt, anions, and cations is further facilitated under pressurization. This causes the inorganic salt, anions, and cations that have penetrated into the electrically conductive rubber body to suppress a potential variation due to the polarization voltage in the electrically conductive rubber body to thereby enable potential variation noise to be reduced. Additionally, the inorganic salt does not exist as masses such as particles in the inorganic salt-containing solution, and thus, the inorganic salt efficiently acts on suppression of the polarization voltage. Additionally, measures for suppression of the polarization voltage can be achieved by means of inexpensive materials and simple steps, and thus, the production cost of the bioelectrode also can be reduced. Furthermore, since inorganic salts have high safety to the human body, the safety of products of the bioelectrode is also improved.

(1) A bioelectrode including an electrically conductive rubber body containing a silicone rubber, a silver powder, and an inorganic salt.

(2) The bioelectrode according to the above (1), wherein, the inorganic salt is at least one inorganic salt selected from the group consisting of sodium chloride, potassium chloride, lithium chloride, calcium chloride, magnesium chloride, sodium sulfate, potassium sulfate, lithium sulfate, calcium sulfate, magnesium sulfate, sodium carbonate, potassium carbonate, lithium carbonate, calcium carbonate, and magnesium carbonate.

(3) The bioelectrode according to the above (1), wherein
the bioelectrode further has an electrically conductive substrate, the electrically conductive rubber body is provided on the electrically conductive substrate, and the electrically conductive rubber body has a layered shape.

(4) The bioelectrode according to the above (1), wherein the electrically conductive rubber body has a brush-like shape.

EXAMPLES

Hereinafter, the present disclosure will be described more in detail based on examples conducted to clarify the effects of the present disclosure. Note that the present disclosure is not limited by the following examples and comparative examples in any way.

Production of Electrically Conductive Substrate

Kneaded were 100 parts by mass of an electrically conductive silicone rubber (trade name: "KE-3801M-U"; containing carbon black, manufactured by Shin-Etsu Chemical Co., Ltd.) and 1.0 parts by mass of a crosslinking agent (trade name "C-8A"; 2,5-dimethyl-2,5-bis(t-butylperoxy) hexane content: 80% by mass, manufactured by Shin-Etsu Chemical Co., Ltd.) in a kneader for 10 minutes. Then, the mixture was kneaded with a roll for three minutes to obtain a material (carbon black content: 6% by volume). Thereafter, the obtained material was press-crosslinked (primary-crosslinked) at 180° C. for four minutes. Then, the primary-crosslinked product was secondary-crosslinked at 230° C. for five hours to thereby obtain a sheet-form electrically conductive substrate having a thickness of 1.0 mm formed by the electrically conductive silicone rubber.

Production of Electrically Conductive Rubber Body 1

A silver paste was obtained by centrifuging and stirring 100 parts by mass of a silicone rubber (trade name: "KE-106", manufactured by Shin-Etsu Chemical Co., Ltd.), 10 parts by mass of a curing agent (trade name: "CAT-RG", manufactured by Shin-Etsu Chemical Co., Ltd.), 165 parts by mass of a silver powder A (trade name: "FA-D-3", manufactured by DOWA Electronics Materials Co., Ltd.), 165 parts by mass of a silver powder B (trade name: "G-35", manufactured by DOWA Electronics Materials Co., Ltd.), 10 parts by mass of a dispersant A (trade name: "KF-6015", manufactured by Shin-Etsu Chemical Co., Ltd.), and 10 parts by mass of a dispersant B (trade name "KF-6106", manufactured by Shin-Etsu Chemical Co., Ltd.). Thereafter, the silver paste was applied by screen printing on the electrically conductive substrate produced as described above. Then, the silver paste was cured at 150° C. for 30 minutes to thereby produce an electrically conductive rubber body 1. The formulation of the electrically conductive rubber body 1 is shown in the following Table 1.

Production of Electrically Conductive Rubber Body 2

An electrically conductive rubber body 2 was produced in the same manner as for the electrically conductive rubber body 1 except that the dispersant A and the dispersant B were not used. The formulation of the electrically conductive rubber body 2 is shown in the following Table 1.

TABLE 1

| Components | Electrically conductive rubber body 1 (parts by mass) | Electrically conductive rubber body 2 (parts by mass) |
| --- | --- | --- |
| Silicone rubber | 100 | 100 |
| Curing agent | 10 | 10 |
| Silver powder A | 165 | 165 |
| Silver powder B | 165 | 165 |
| Dispersant A | 10 | — |
| Dispersant B | 10 | — |

Example 1

The electrically conductive substrate with which the electrically conductive rubber body 1 was produced as described above was subjected to a salt water treatment by immersing the substrate in a 1% by mass sodium chloride aqueous solution (hereinafter, the solution may be referred to as the "salt water") at 1 atm and 80° C. for an hour and then dried to produce a bioelectrode. The conditions for the salt water treatment are shown in the following Table 2.

Example 2

A bioelectrode was produced in the same manner as in Example 1 except that the immersion time in the 1% by mass sodium chloride aqueous solution during the salt water treatment was set to two hours. The conditions for the salt water treatment are shown in the following Table 2.

Example 3

A bioelectrode was produced in the same manner as in Example 1 except that the immersion time in the 1% by mass sodium chloride aqueous solution during the salt water treatment was set to three hours. The conditions for the salt water treatment are shown in the following Table 2.

Example 4

A bioelectrode was produced in the same manner as in Example 1 except that the immersion time in the 1% by mass sodium chloride aqueous solution during the salt water treatment was set to four hours. The conditions for the salt water treatment are shown in the following Table 2.

Example 5

A bioelectrode was produced in the same manner as in Example 1 except that the temperature of the 1% by mass sodium chloride aqueous solution was set to 121° C. and the pressure was set to 2 atm during immersion in the 1% by mass sodium chloride aqueous solution in the salt water treatment. The conditions for the salt water treatment are shown in the following Table 2.

Example 6

A bioelectrode was produced in the same manner as in Example 5 except that the electrically conductive substrate with which the electrically conductive rubber body 2 was produced was subjected to the salt water treatment. The conditions for the salt water treatment are shown in the following Table 2.

Comparative Example 1

A bioelectrode was produced in the same manner as in Example 1 except that the temperature of the 1% by mass sodium chloride aqueous solution was set to 25° C. during immersion in the 1% by mass sodium chloride aqueous solution in the salt water treatment. The conditions for the salt water treatment are shown in the following Table 2.

Comparative Example 2

A bioelectrode was produced in the same manner as in Example 2 except that the temperature of the 1% by mass sodium chloride aqueous solution was set to 25° C. during immersion in the 1% by mass sodium chloride aqueous solution in the salt water treatment. The conditions for the salt water treatment are shown in the following Table 2.

Comparative Example 3

A bioelectrode was produced in the same manner as in Example 3 except that the temperature of the 1% by mass sodium chloride aqueous solution was set to 25° C. during immersion in the 1% by mass sodium chloride aqueous solution in the salt water treatment. The conditions for the salt water treatment are shown in the following Table 2.

Comparative Example 4

A bioelectrode was produced in the same manner as in Example 4 except that the temperature of the 1% by mass sodium chloride aqueous solution was set to 25° C. during immersion in the 1% by mass sodium chloride aqueous solution in the salt water treatment. The conditions for the salt water treatment are shown in the following Table 2.

Comparative Example 5

A bioelectrode was produced in the same manner as in Comparative Example 1 except that the electrically conductive substrate with which the electrically conductive rubber body 2 was produced was subjected to the salt water treatment. The conditions for the salt water treatment are shown in the following Table 2.

TABLE 2

| | Type of electrically conductive rubber body | Sodium chloride concentration in salt water (% by mass) | Temperature of salt water (° C.) | Pressure during salt water treatment (atm) | Time of salt water treatment (hours) |
|---|---|---|---|---|---|
| Example 1 | Electrically conductive rubber body 1 | 1 | 80 | 1 | 1 |
| Example 2 | Electrically conductive rubber body 1 | 1 | 80 | 1 | 2 |
| Example 3 | Electrically conductive rubber body 1 | 1 | 80 | 1 | 3 |
| Example 4 | Electrically conductive rubber body 1 | 1 | 80 | 1 | 4 |
| Example 5 | Electrically conductive rubber body 1 | 1 | 121 | 2 | 1 |
| Example 6 | Electrically conductive rubber body 2 | 1 | 121 | 2 | 1 |
| Comparative Example 1 | Electrically conductive rubber body 1 | 1 | 25 | 1 | 1 |
| Comparative Example 2 | Electrically conductive rubber body 1 | 1 | 25 | 1 | 2 |
| Comparative Example 3 | Electrically conductive rubber body 1 | 1 | 25 | 1 | 3 |
| Comparative Example 4 | Electrically conductive rubber body 1 | 1 | 25 | 1 | 4 |
| Comparative Example 5 | Electrically conductive rubber body 2 | 1 | 25 | 1 | 1 |

Evaluation Method

Figure 9:
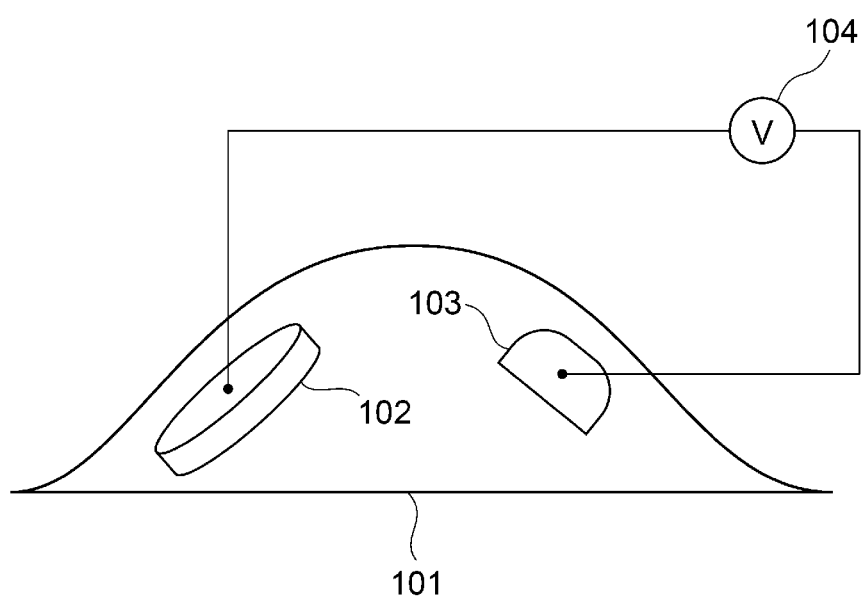
FIG. 9 is an explanatory view of a potentiometry test.

FIG. 9 is an explanatory view of a potentiometry test. As shown in FIG. 9, in the potentiometry test, a bioelectrode 102 produced in each of Examples and Comparative Examples described above and a commercially available silver chloride electrode (trade name: "electroencephalographic dish electrode", manufactured by Nihon Kohden Corporation) 103 were disposed on an electroencephalographic electrically conductive paste (trade name: "Elefix®", manufactured by Nihon Kohden Corporation) 101, and the potential difference between the two electrodes was measured for 10 minutes with a multimeter 104. The evaluation results are shown in FIG. 10 to FIG. 13.

Figure 10:
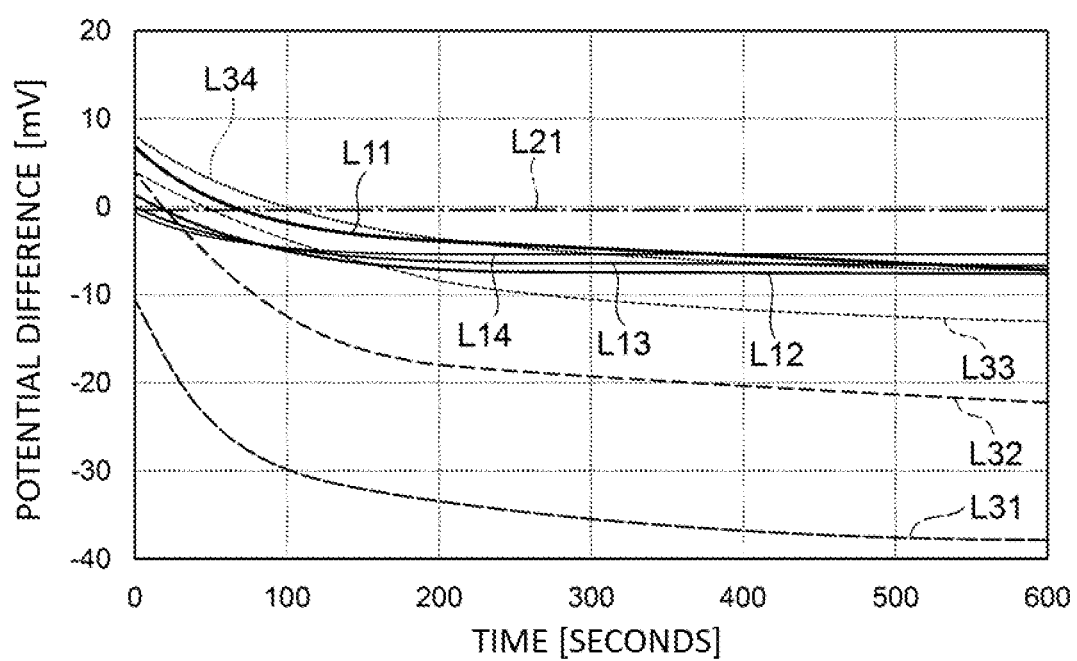
FIG. 10 is a graph showing the measurement results of the potential difference of the bioelectrodes in Examples 1 to 4 and Comparative Examples 1 to 4.
Figure 11:
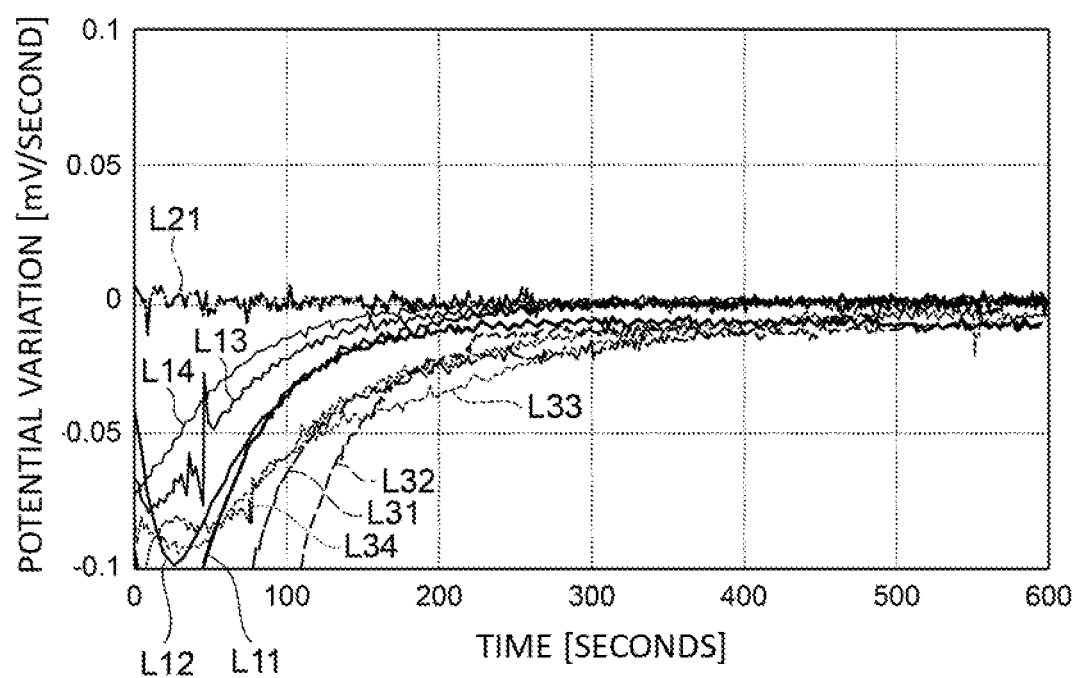
FIG. 11 is a graph showing the measurement results of the potential variation of the bioelectrodes in Examples 1 to 4 and Comparative Examples 1 to 4.

FIG. 10 is a graph showing the measurement results of the potential difference of the bioelectrodes, and FIG. 11 is a graph showing the measurement results of the potential variation of the bioelectrodes. Note that, in FIG. 10, the vertical axis indicates the potential difference and the horizontal axis indicates the measurement time, and in FIG. 11, the vertical axis indicates the potential variation and the horizontal axis indicates the measurement time. Additionally, each line in FIGS. 10 and 11 has the following meaning. The measurement results obtained by using the bioelectrodes of Examples 1, 2, 3, and 4 are represented by solid lines L11, L12, L13, and L14, respectively. The measurement result of Reference Example, in which a silver electrode was connected, instead of the bioelectrode 102, to an electroencephalographic electrically conductive paste 201, is represented by a dot-dashed line L21. The measurement results obtained by using the bioelectrodes of Comparative Examples 1, 2, 3, and 4 are represented by broken lines L31, L32, L33, and L34, respectively. Additionally, the potential difference shown in FIGS. 10 and 11 is a comparison with respect to that of Reference Example.

As shown in FIG. 10, in all of Examples 1 to 4, in which the electrically conductive rubber body 1 was subjected to a salt water treatment at a high temperature (80° C.), the potential difference was stabilized in 300 seconds after the start of the measurement, and results comparable to that of Reference Example was obtained. In contrast, in Comparative Examples 1 to 4, in which the salt water treatment was conducted at a low temperature (25° C.), the change in the potential difference tended to decrease as the treatment time extended. However, even in the case where the salt water treatment was conducted for four hours (Comparative Example 4), the variation in the potential difference did not subside even when 600 seconds passed since the start of the measurement.

Additionally, as shown in FIG. 11, in all of Examples 1 to 4, in which the electrically conductive rubber body 1 was subjected to the salt water treatment at a high temperature (80° C.), after 300 seconds passed since the start of the measurement, the potential variation from the potential at one second after the start of the measurement reached substantially 0, substantially no potential variation noise occurred, and results comparable to that of Reference Example was obtained. In contrast, in Comparative Examples 1 to 4, in which the salt water treatment was conducted at a low temperature (25° C.), the potential variation tended to decrease as the salt water treatment time extended. However, even in the case where the salt water treatment was conducted for four hours (Comparative Example 4), the potential variation did not subside even when 600 seconds passed since the start of the measurement, and potential variation noise occurred.

Figure 12:
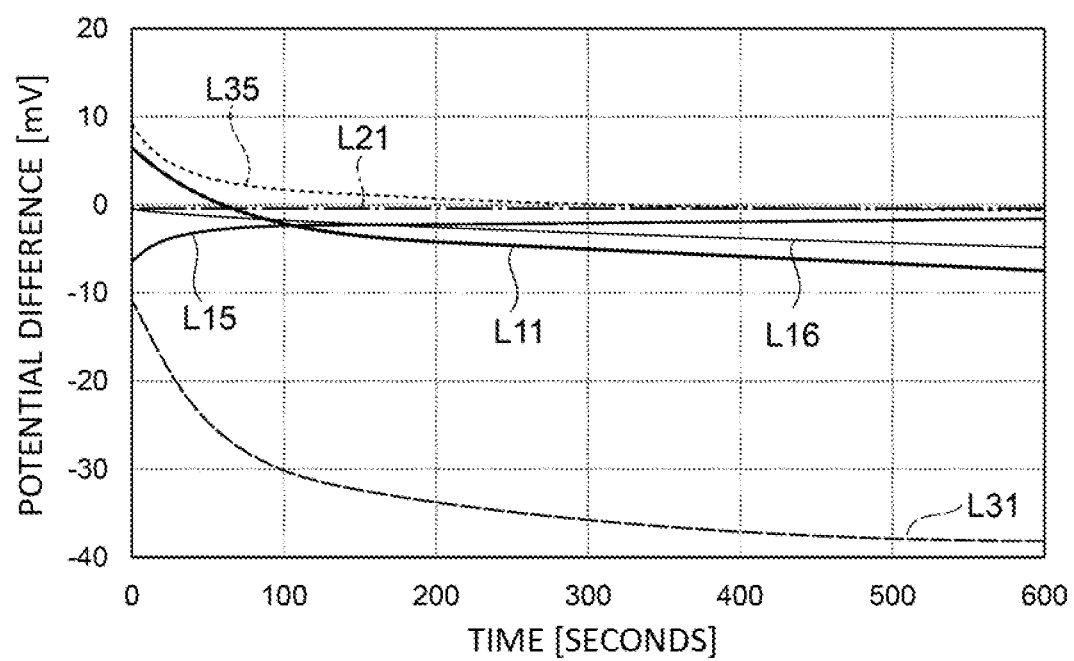
FIG. 12 is a graph showing the measurement results of the potential difference of the bioelectrodes in Examples 1, 5, and 6 and Comparative Examples 1 and 5.
Figure 13:
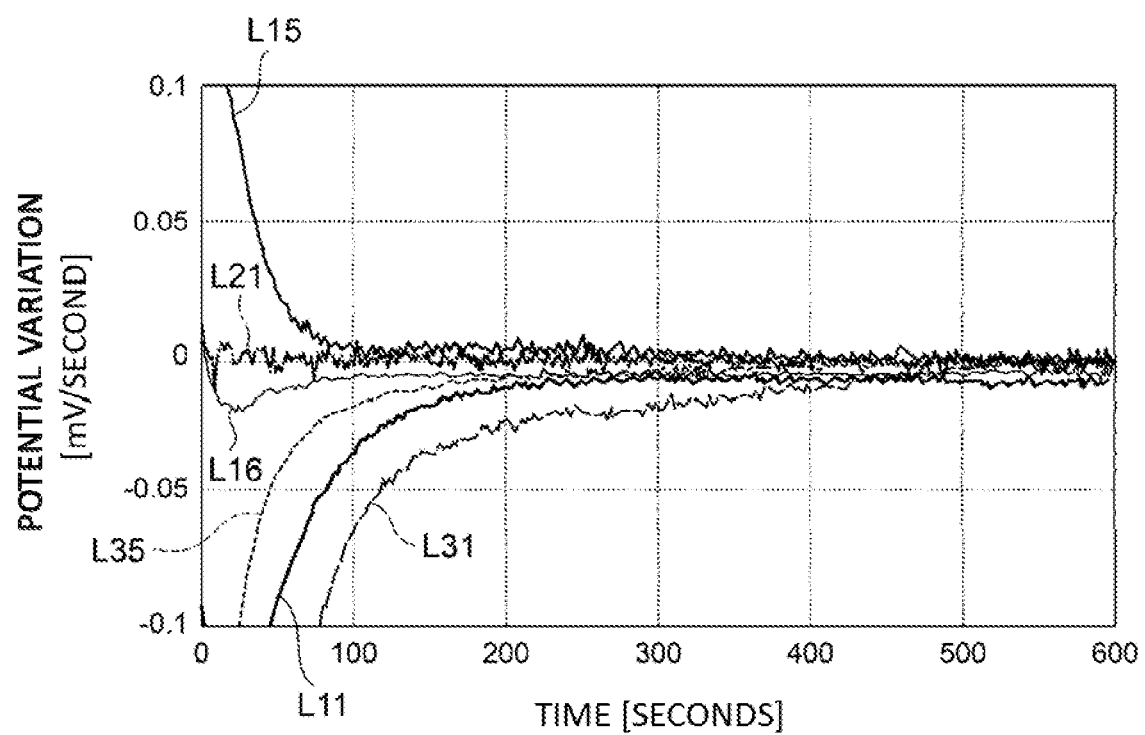
FIG. 13 is a graph showing the measurement results of the potential variation of the bioelectrodes in Examples 1, 5, and 6 and Comparative Examples 1 and 5.

FIG. 12 is a graph showing the measurement results of the potential difference of the bioelectrodes, and FIG. 13 is a graph showing the measurement results of the potential variation of the bioelectrodes. Note that, in FIG. 12, as in FIG. 10, the vertical axis indicates the potential difference and the horizontal axis indicates the measurement time, and, in FIG. 13, as in FIG. 11, the vertical axis indicates the potential variation and the horizontal axis indicates the measurement time. Additionally, each line in FIGS. 12 and 13 has the following meaning. The measurement results obtained by using the bioelectrodes of Examples 1, 5, and 6 are represented by solid lines L11, L15, and L16, respectively. The measurement result of Reference Example, in which a silver electrode was connected, instead of the bioelectrode 102, to an electroencephalographic electrically conductive paste 201, is represented by a dot-dashed line L21. The measurement results obtained by using the bioelectrodes of Comparative Examples 1 and 5 are represented by broken lines L31 and L35, respectively. Additionally, the potential difference shown in FIGS. 12 and 13 is a comparison with respect to that of Reference Example.

As shown in FIG. 12, in Examples 5 and 6, in which the electrically conductive rubber bodies 1 and 2 were subjected to the salt water treatment at a high temperature (121° C.) and a high pressure (2 atm), the potential difference was stabilized in 200 seconds after the start of the measurement, and results comparable to that of Reference Example were given. The results were satisfactory with respect to that of Example 1, in which the salt water treatment was conducted at a high temperature (80° C.) and normal pressure (1 atm). In contrast, in Comparative Example 5, in which the electrically conductive rubber body 2 was subjected to the salt water treatment at normal temperature (25° C.) and normal pressure (1 atm), the potential difference was stabilized in 350 seconds after the start of the measurement to thereby become comparable to that of Reference Example, and a satisfactory result was obtained with respect to that of Comparative Example 1, in which the electrically conductive rubber body 1 was used. Meanwhile, the result of Comparative Example 5 required a longer time for stabilization of the potential difference, in comparison with that of Example 5. Additionally, as shown in FIG. 13, in both Examples 5 and 6, in which the electrically conductive rubber bodies 1 and 2 were subjected to the salt water treatment at a high temperature (121° C.) and under pressurization (2 atm), when 100 seconds passed since the start of the measurement, the potential variation per one second reached substantially 0, and as a result, substantially no potential variation noise occurred. The result was comparable to that of Reference Example, and further satisfactory in comparison with that of Example 1, in which the electrically conductive rubber body 1 was subjected to the salt water treatment at a high temperature (80° C.) and normal pressure (1 atm). In contrast, in Comparative Example 5, in which the electrically conductive rubber body 2 was subjected to the salt water treatment at a low temperature (25° C.), the potential difference was stabilized in 350 seconds after the start of the measurement to thereby become comparable to that of Reference Example, and a satisfactory result was obtained with respect to that of Comparative Example 1, in which the electrically conductive rubber body 1 was used. Meanwhile, the result of Comparative Example 5 required a significantly longer time for stabilization of the potential difference in comparison with those of Examples 5 and 6, and potential variation noise occurred.

As mentioned above, according to Examples 1 to 6 and Comparative Examples 1 to 5 described above, it can be seen that used is the bioelectrode of which electrically conductive rubber body has been subjected to the salt water treatment under a heating condition enables potential variation noise to be reduced as well as used is the bioelectrode of which electrically conductive rubber body has been subjected to the salt water treatment under heating and pressurizing conditions, thereby enabling potential variation noise to be significantly reduced.

Example 7

A silver paste was obtained by centrifuging and stirring 100 parts by mass of a silicone rubber (trade name: "KE-106", manufactured by Shin-Etsu Chemical Co., Ltd.), 10 parts by mass of a curing agent (trade name: "CAT-RG", manufactured by Shin-Etsu Chemical Co., Ltd.), 165 parts by mass of a silver powder B (trade name: "G-35", manufactured by DOWA Electronics Materials Co., Ltd.), 165 parts by mass of a silver powder C (trade name: "FA-2-3", manufactured by DOWA Electronics Materials Co., Ltd.), 10 parts by mass of a dispersant A (trade name: "KF-6015", manufactured by Shin-Etsu Chemical Co., Ltd.), and 10 parts by mass of a dispersant B (trade name "KF-6106", manufactured by Shin-Etsu Chemical Co., Ltd.). Thereafter, the obtained silver paste was used and press-molded in a brush shape (height of the projection body 22a: 7 mm, diameter of the main body portion 221a of the projection body 22a: 4 mm) as illustrated in FIGS. 5 to 8. The silver paste in a press-molded state was primary-crosslinked at 150° C. for 3 minutes. Then, the primary-crosslinked product was secondary-crosslinked at 150° C. for 30 minutes to obtain an electrically conductive rubber body before a salt water treatment. Thereafter, the salt water treatment was conducted by immersing the obtained electrically conductive rubber body in a 10% by mass sodium chloride aqueous solution (hereinafter, the solution may be referred to as the "salt water") under conditions of a high temperature (121° C.) and a high pressure (2 atm) for an hour to produce a bioelectrode. The formulation of components of the electrically conductive rubber body are shown in Table 3, and the conditions for the salt water treatment are shown in the following Table 4.

Comparative Example 6

A bioelectrode was produced in the same manner as in Example 7 except that the temperature of 10% by mass sodium chloride aqueous solution was set to 25° C., the pressure was set to 1 atm, and the immersion time was set to 8 hours during immersion in the 10% by mass sodium chloride aqueous solution in the salt water treatment. The formulation of components of the electrically conductive rubber body are shown in Table 3, and the conditions for the salt water treatment are shown in the following Table 4.

TABLE 3

| Components | Example 7 (parts by mass) | Comparative Example 6 (parts by mass) |
| --- | --- | --- |
| Silicone rubber | 100 | 100 |
| Curing agent | 10 | 10 |
| Silver powder B | 165 | 165 |
| Silver powder C | 165 | 165 |
| Dispersant A | 10 | 10 |
| Dispersant B | 10 | 10 |

TABLE 4

| | Concentration of sodium chloride in salt water (% by mass) | Temperature of salt water (° C.) | Pressure during salt water treatment (atm) | Time of salt water treatment (hours) |
|---|---|---|---|---|
| Example 7 | 10 | 121 | 2 | 1 |
| Comparative Example 6 | 10 | 25 | 1 | 8 |

Evaluation Method

Figure 14:
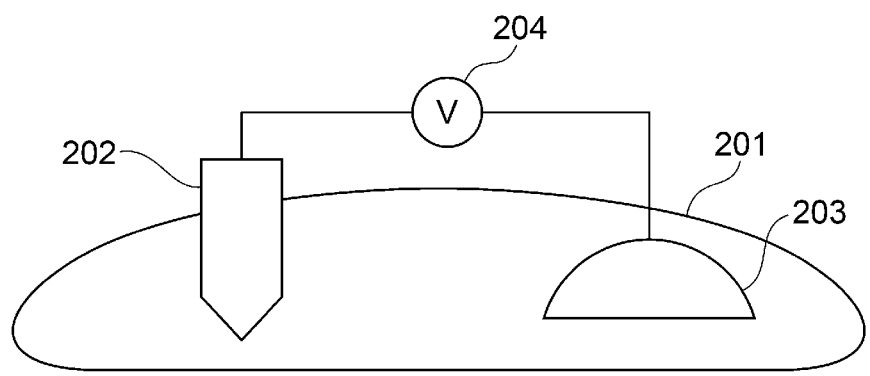
FIG. 14 is an explanatory view of a polarization voltage measurement test.

FIG. 14 is an explanatory view of a polarization voltage measurement test. As shown in FIG. 14, in the polarization voltage measurement test, a bioelectrode 202 produced in Example 7 and Comparative Example 6 described above and a commercially available silver chloride electrode (trade name: "electroencephalographic dish electrode", manufactured by Nihon Kohden Corporation) 203 were caused to contact onto an electroencephalographic electrically conductive paste containing chloride ions (trade name: "Elefix® Z-401CE", manufactured by Nihon Kohden Corporation) 201. The potential difference between the two electrodes was measured for 15 minutes with a multimeter 204 to evaluate the polarization voltage. The evaluation results are shown in FIG. 15 and FIG. 16.

Figure 15:
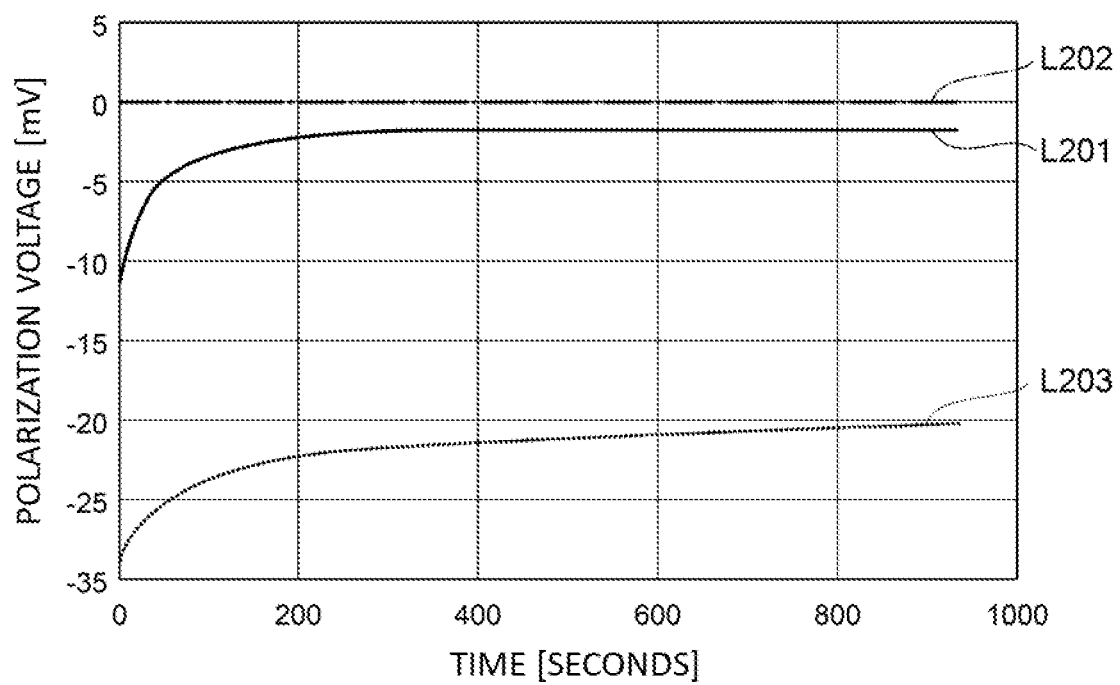
FIG. 15 is a graph showing the measurement results of the polarization voltage of the bioelectrodes in Example 7 and Comparative Example 6.
Figure 16:
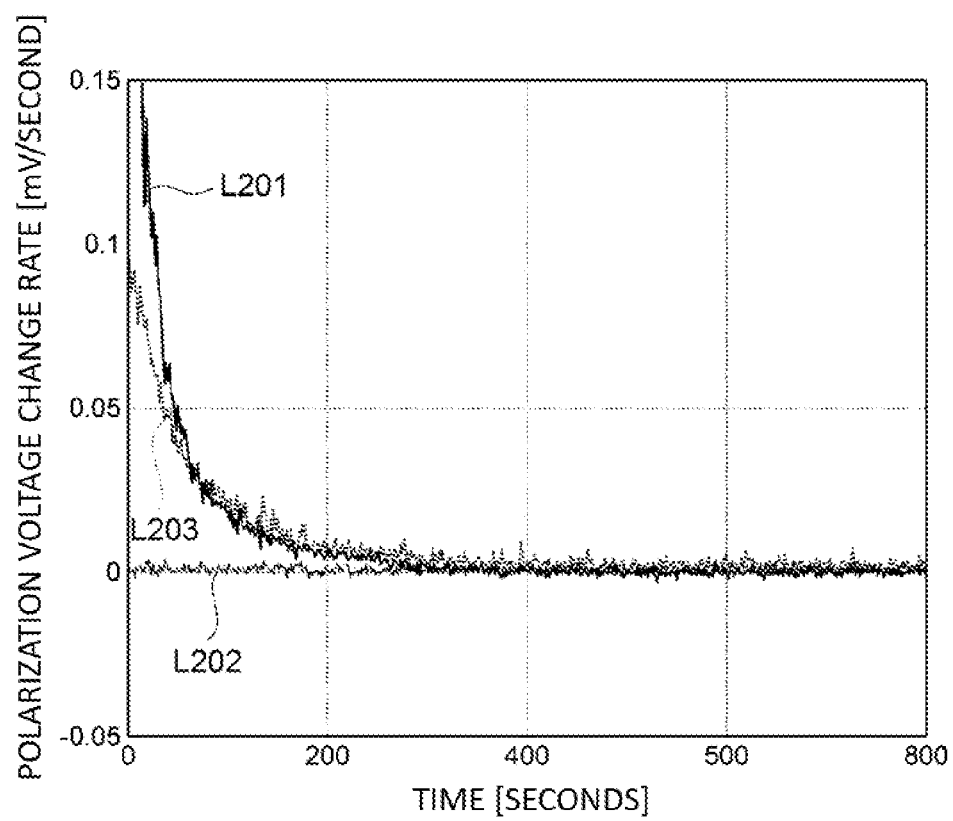
FIG. 16 is a graph showing the measurement results of the polarization voltage change rate of the bioelectrodes in Example 7 and Comparative Example 6.

FIG. 15 is a graph showing the measurement results of the polarization voltage, and FIG. 16 is a graph showing the measurement results of the polarization voltage change rate of the bioelectrodes. Note that, in FIG. 15, the vertical axis indicates the polarization voltage and the horizontal axis indicates the measurement time, and in FIG. 16, the vertical axis indicates the polarization voltage change rate, and the horizontal axis indicates the measurement time. Additionally, each line in FIGS. 15 and 16 has the following meaning. The measurement result obtained by using the bioelectrode of Example 7 is represented by a solid line L201. The measurement result of Reference Example, in which a silver electrode was connected, instead of the bioelectrode 202, to an electroencephalographic electrically conductive paste 201, is represented by a dot-dashed line L202. The measurement result obtained by using the bioelectrode of Comparative Examples 6 is represented by a broken line L203.

As shown in FIG. 15, the polarization voltage of the bioelectrode of Example 7 reached −3 mV to −2 mV in a short time after the start of the measurement, and a measurement result comparable to that of Reference Example was given. In contrast, the polarization voltage of the bioelectrode of Comparative Example 6 was of the order of −25 mV to −20 mV even when 800 seconds passed after the start of the measurement, and resulted a significant increase with respect to that of the bioelectrode of Example 7. Also, in the bioelectrode of Example 7, the polarization voltage was stabilized in 300 second after the start of the measurement. In contrast, in the bioelectrode of Comparative Example 6, a measurement result was given in which the polarization voltage was not stabilized during the measurement and gradually increased even when 300 seconds to 900 seconds passed after the start of the measurement. Additionally, as shown in FIG. 16, the polarization voltage change rate of the bioelectrode of Example 7 stabilized at approximately 0, in 300 second after the start of the measurement, and a measurement result comparable to that of Reference Example was given. In contrast, the polarization voltage change rate of the bioelectrode of Comparative Example 6 was at approximately 0 and did not stabilize even when 300 seconds passed after the start of the measurement, resulting in repetitive increases and decreases.

As mentioned above, according to Example 7 described above, it can be found that a bioelectrode can be achieved which has stabilizing performance equivalent to or higher than that of the bioelectrode of Comparative Example 6, in which the salt water treatment was conducted under normal temperature and normal pressure conditions for 8 hours, and additionally gives a result equivalent to that of Reference example, in which a silver/silver chloride electrode was used.

As described hereinabove, bioelectrodes obtained by the production method of the present disclosure can be suitably used particularly in each of fields of medical measuring apparatuses, wearable information apparatuses, game devices, brain-machine interfaces, medical care, care, welfare, automatic cruising, and electronics wiring.

What is claimed is:

1. A method for producing a bioelectrode comprising:
   forming an electrically conductive rubber body containing a silicone rubber and a silver powder; and
   immersing the electrically conductive rubber body in an inorganic salt-containing solution at 100° C. or more and 150° C. or less under a pressure of 2 atm or more and 3 atm or less.

2. The method for producing a bioelectrode according to claim 1, wherein the inorganic salt-containing solution contains at least one inorganic salt selected from the group consisting of sodium chloride, potassium chloride, lithium chloride, calcium chloride, magnesium chloride, sodium sulfate, potassium sulfate, lithium sulfate, calcium sulfate, magnesium sulfate, sodium carbonate, potassium carbonate, lithium carbonate, calcium carbonate, and magnesium carbonate.

3. The method for producing a bioelectrode according to claim 1, wherein, in forming the electrically conductive rubber body, an electrically conductive rubber body is formed as a layer.

4. The method for producing a bioelectrode according to claim 1, wherein, in forming the electrically conductive rubber body, an electrically conductive rubber body is formed as a brush.

* * * * *